US010856922B2

(12) United States Patent
Loke et al.

(10) Patent No.: US 10,856,922 B2
(45) Date of Patent: Dec. 8, 2020

(54) SPINAL IMPLANT SYSTEM AND METHOD

(71) Applicant: Warsaw Orthopedic, Inc, Warsaw, IN (US)

(72) Inventors: Robert M. Loke, Memphis, TN (US); Julien J Prevost, Memphis, TN (US); Thomas J. Stinchfield, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 26 days.

(21) Appl. No.: 15/616,665

(22) Filed: Jun. 7, 2017

(65) Prior Publication Data
US 2018/0353220 A1 Dec. 13, 2018

(51) Int. Cl.
*A61B 17/70* (2006.01)
*A61B 17/88* (2006.01)
*A61B 17/86* (2006.01)
A61B 17/34 (2006.01)
A61B 90/00 (2016.01)
A61B 17/00 (2006.01)

(52) U.S. Cl.
CPC ...... *A61B 17/8811* (2013.01); *A61B 17/7032* (2013.01); *A61B 17/7098* (2013.01); *A61B 17/864* (2013.01); *A61B 17/3472* (2013.01); *A61B 17/7037* (2013.01); *A61B 17/863* (2013.01); *A61B 2017/00455* (2013.01); *A61B 2090/0811* (2016.02)

(58) Field of Classification Search
CPC .......................................... A61B 17/70–7046
See application file for complete search history.

(56) References Cited

U.S. PATENT DOCUMENTS

| | | | | |
|---|---|---|---|---|
| 6,210,376 B1 * | 4/2001 | Grayson | ............ | A61B 17/3472 604/264 |
| 8,062,270 B2 * | 11/2011 | Sweeney | ............ | A61B 17/3472 604/264 |
| 8,574,273 B2 * | 11/2013 | Russell | .............. | A61B 17/0401 606/304 |
| 8,821,506 B2 * | 9/2014 | Mitchell | ............... | A61M 31/00 606/271 |
| 8,945,193 B2 | 2/2015 | Kirschman | | |
| 8,992,587 B2 | 3/2015 | Kirschman | | |
| 9,078,701 B2 | 7/2015 | Thalgott et al. | | |
| 9,265,540 B2 | 2/2016 | Kirschman | | |
| 9,333,018 B2 | 5/2016 | Russell et al. | | |
| 9,592,081 B2 | 3/2017 | Thalgott et al. | | |
| 9,603,644 B2 * | 3/2017 | Sweeney | .............. | A61B 17/864 |
| 2004/0225292 A1 * | 11/2004 | Sasso | ................. | A61B 17/8615 606/916 |

(Continued)

FOREIGN PATENT DOCUMENTS

WO 2014149746 A1 9/2014

*Primary Examiner* — Nicholas J Plionis
*Assistant Examiner* — Steven J Cotroneo
(74) *Attorney, Agent, or Firm* — Sorell, Lenna & Schmidt, LLP

(57) ABSTRACT

A bone fastener includes a shaft. The shaft includes a wall that defines a longitudinal cavity and a plurality of openings in communication therewith. The openings are disposed in axial alignment along the shaft and the wall is closed exclusive of the openings. In some embodiments, systems, spinal constructs, surgical instruments and methods are disclosed.

20 Claims, 6 Drawing Sheets

(56) References Cited

U.S. PATENT DOCUMENTS

| | | | |
|---|---|---|---|
| 2005/0015060 A1* | 1/2005 | Sweeney | A61B 17/864 604/264 |
| 2005/0015061 A1* | 1/2005 | Sweeney | A61B 17/7061 604/264 |
| 2005/0059972 A1* | 3/2005 | Biscup | A61B 17/686 606/308 |
| 2010/0137875 A1* | 6/2010 | Marino | A61B 17/7002 606/104 |
| 2011/0190825 A1 | 8/2011 | Thalgott et al. | |
| 2012/0022603 A1 | 1/2012 | Kirschmann | |
| 2012/0203286 A1* | 8/2012 | Armstrong | A61B 17/866 606/304 |
| 2014/0058461 A1* | 2/2014 | Black | A61B 17/863 606/314 |
| 2015/0157366 A1 | 6/2015 | Kirschmann | |
| 2015/0196371 A1* | 7/2015 | Westover | A61C 8/0022 433/174 |
| 2016/0008039 A1 | 1/2016 | Thalgott et al. | |

* cited by examiner

SPINAL IMPLANT SYSTEM AND METHOD

TECHNICAL FIELD

The present disclosure generally relates to medical devices for the treatment of spinal disorders, and more particularly to a surgical implant system including a bone fastener and a related method.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener includes a shaft. The shaft includes a wall that defines a longitudinal cavity and a plurality of openings in communication therewith. The openings are disposed in axial alignment along the shaft and the wall is closed exclusive of the openings. In some embodiments, systems, spinal constructs, spinal implants, surgical instruments and methods are disclosed.

In one embodiment, the bone fastener includes a head and a threaded shaft. The shaft includes a wall that defines an inner surface and an outer surface. The inner surface defines a longitudinal cavity and a plurality of equally spaced lateral fenestrations disposed in a serial orientation adjacent a distal portion of the shaft. The wall is closed exclusive of the fenestrations.

In one embodiment, the bone fastener includes an implant receiver and a shaft. The shaft includes a wall that defines a longitudinal cavity and a plurality of openings in communication therewith. The shaft includes indicia of orientation of the openings for deployment of an agent with tissue.

BRIEF DESCRIPTION OF THE DRAWINGS

The present disclosure will become more readily apparent from the specific description accompanied by the following drawings, in which.

DETAILED DESCRIPTION

Figure 1:
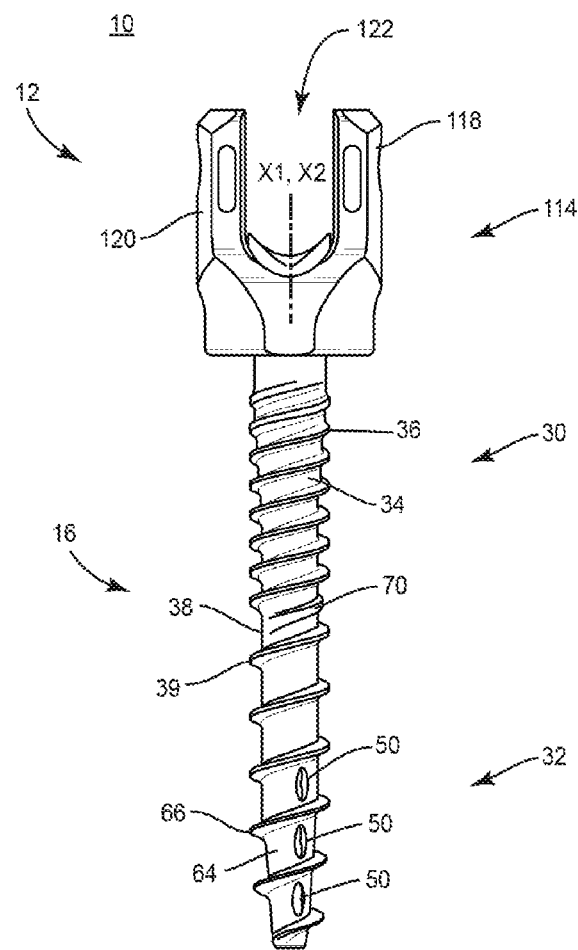
FIG. 1 is a side view of components of one embodiment of a system in accordance with the principles of the present disclosure.
Figure 2:
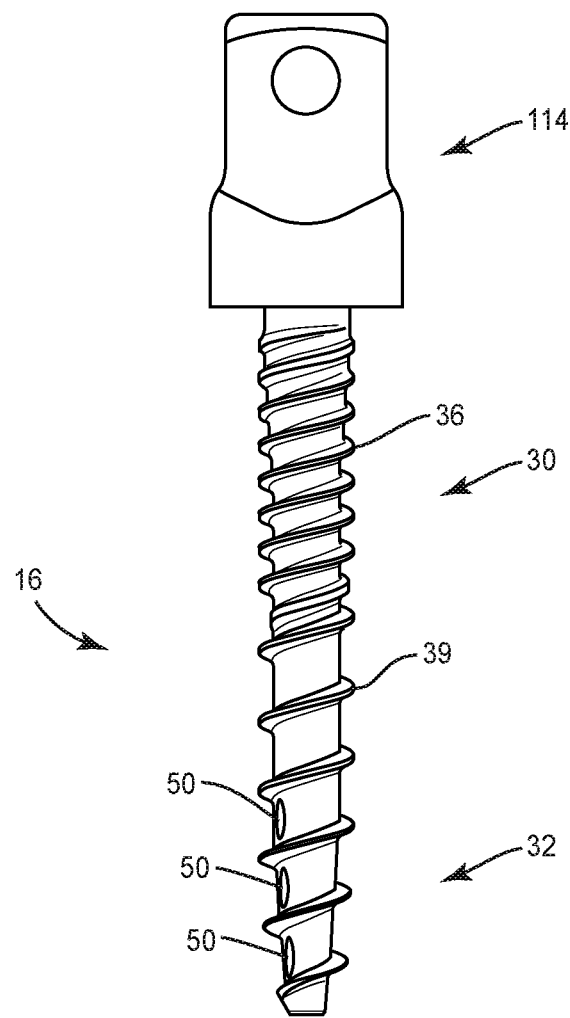
FIG. 2 is a side view of components of one embodiment of a system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone fastener and a method for treating one or more spinal disorders. In some embodiments, the spinal implant system includes an implant comprising a bone screw having a fenestrated shaft.

In some embodiments, the surgical system of the present disclosure comprises a spinal implant, such as, for example, a bone screw including one or a plurality of openings configured to expel a biologic or agent in a selected orientation with tissue. In some embodiments, the spinal implant includes a fenestrated bone screw configured for controlled cement placement.

In some embodiments, the surgical system of the present disclosure comprises a spinal implant, such as, for example, a bone screw including one or a plurality of openings configured to disperse a biologic or agent relative to the axis of the bone screw to reduce a risk of complications to a patient, for example, extravasation adjacent areas of bone degeneration. In some embodiments, the bone screw includes fenestrations disposed along only one side of the bone screw to control the direction that the biologic or agent is placed with tissue. In some embodiments, the bone screw includes fenestrations disposed along only one side of the bone screw to provide a uni-directional cement deployment and enable more controlled placement. In some embodiments, the bone screw includes fenestrations disposed along the same side of the bone screw to allow a surgeon to have directional control of the deployment of the cement to avoid areas of diminished bone quality. In some embodiments, the bone screw includes fenestrations that provide directional control of the cement deployment.

In some embodiments, the surgical system of the present disclosure comprises a spinal implant, such as, for example, a fenestrated bone screw that is engageable with tissue surfaces of one or more vertebral levels. In some embodiments, the bone screw includes a proximal member, such as, for example, an implant receiver and a distal member, such as, for example, a threaded shaft. In some embodiments, the bone screw can include various configurations, such as, for example, a posted screw, a pedicle screw, a bolt, a bone screw for a lateral plate, an interbody screw, a uni-axial screw (UAS), a fixed angle screw (FAS), a multi-axial screw (MAS), a side loading screw, a sagittal adjusting screw (SAS), a transverse sagittal adjusting screw (TSAS), an awl tip (ATS), a dual rod multi-axial screw (DRMAS), midline lumbar fusion screw and/or a sacral bone screw.

In some embodiments, the surgical system of the present disclosure comprises a bone screw including a fenestrated shaft that maintains cortical purchase. In some embodiments, the bone screw includes fenestrations that are disposed proximally from a distal tip of the shaft. In some embodiments, the bone screw includes a cannulated portion configured to extend a distance along the shaft such that the distal tip is solid. In some embodiments, the positioning of the cannulated portion along a distance of the shaft is configured to prevent leakage of cement outside a vertebral body. In some embodiments, the distal tip includes various configurations to facilitate engagement with tissue. In some embodiments, the surgical system of the present disclosure includes a bone screw that enhances fixation with vertebrae and is used with a biologic or agent, for example, bone cement (PMMA).

In some embodiments, the surgical system of the present disclosure comprises a bone screw including indicia and/or a directional indicator of orientation of the one or plurality of openings. In some embodiments, the indicia and/or directional indicator displays the orientation of deployment of a biologic or an agent from the one or plurality of openings with tissue. In some embodiments, the indicia and/or directional indicator displays the orientation of a uni-directional biologic or agent deployment, which enables more controlled placement of the biologic or agent. In some embodiments, the indicia and/or directional indicator includes a marking, notch, slot, bead, detent, bump, print, label, score, color coding and/or cavity disposed on a head of a bone screw shaft. In some embodiments, the indicia and/or directional indicator may be disposed with a surgical instrument engageable with the bone screw and aligned with the one or plurality of openings and/or indicia disposed on the head of a bone screw shaft. In some embodiments, the indicia and/or directional indicator facilitates locating the one or plurality of openings and/or their orientation with tissue.

In some embodiments, the surgical system of the present disclosure comprises a bone screw including one or more groups or arrays of the one or plurality of openings disposed with the bone screw shaft. In some embodiments, the groups or arrays can be spaced apart, parallel, transverse, disposed at a relative angular orientation, axially aligned, in series, offset, staggered and/or perpendicular. In some embodiments, each group or array can include a row or column of one or a plurality of openings. In some embodiments, the bone screw includes a first array of openings and a second array of openings disposed along the bone screw shaft such that the bone screw provides deployment of the biologic or agent to selected tissue, for example, with a selected tissue quadrant disposed about the bone screw shaft. In some embodiments, the bone screw includes a first array of openings disposed along the bone screw shaft at a relative angular orientation of 60 degrees relative to a second array of openings.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions such as maxillofacial and extremities. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-4, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as poly-aetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant, such as, for example, a bone fastener 12. In some embodiments, bone fastener 12 is configured to facilitate selective expulsion of an agent from bone fastener 12 in a uni-directional orientation with tissue. Selective positioning of bone fastener 12 to expel an agent facilitates directional control of the agent into targeted tissue and/or healthier, less degenerated tissue to resist and/or prevent leakage of the agent and to enhance fixation, facilitate bone growth, provide therapy and/or diagnosis, as described herein.

Bone faster 12 includes an elongated shaft 16 and a proximal head 100. Shaft 16 extends along an axis X1 between a proximal portion 30 and a distal tip 32. Portion 30 includes a proximal surface 34 having a thread 36. Thread 36 is oriented with shaft 16 and disposed for engagement with tissue. Portion 30 includes a distal surface 38 having a thread 39. Thread 39 is oriented with shaft 16 and disposed for engagement with tissue. Threads 36, 39 are disposed in a serial orientation along shaft 16.

Thread 36 includes a fine, closely-spaced and/or shallow configuration to facilitate and/or enhance engagement with tissue. In some embodiments, thread 36 includes a smaller pitch or more thread turns per axial distance of shaft 16 relative to thread 39 such that thread 36 provides a stronger fixation with vertebral tissue and/or resists loosening from tissue. In some embodiments, thread 39 includes a greater pitch and an increased lead between thread turns relative to thread 36. In some embodiments, thread 36 is continuous along shaft 16. In some embodiments, thread 39 is continuous along shaft 16.

In some embodiments, threads 36, 39 may be intermittent, staggered, discontinuous and/or may include a single thread turn or a plurality of discrete threads. In some embodiments, other penetrating elements may be located on shaft 16, such as, for example, a nail configuration, barbs, expanding elements, raised elements, ribs, and/or spikes to facilitate engagement of shaft 16 with tissue. In some embodiments, threads 36, 39 may be self-tapping or intermittent.

Figure 4:
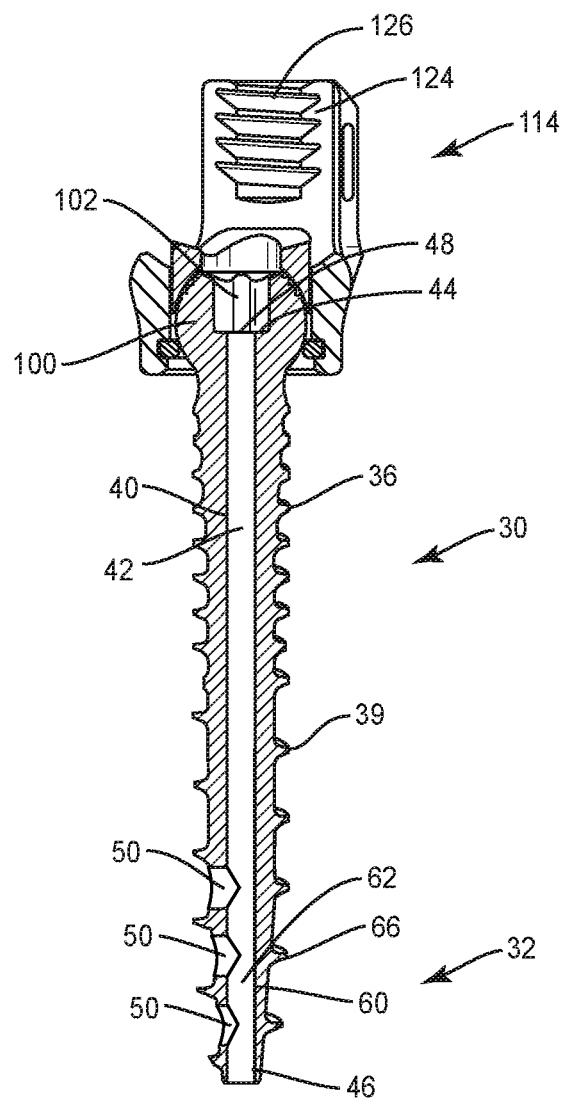
FIG. 4 is a cross section view of components of one embodiment of a system in accordance with the principles of the present disclosure.

Portion 30 includes a wall having an inner surface 40. Surface 40 defines a longitudinal cavity, such as, for example, passageway 42 such that bone fastener 12 includes a cannulated configuration. Passageway 42 extends along axis X1. Passageway 42 is configured to direct and/or guide an agent disposed therein into a vertebral body to enhance fixation, facilitate bone growth, provide therapy and/or diagnosis, as described herein. In some embodiments, passageway 42 is configured to direct and/or guide bone cement into a vertebral body to facilitate fixation of bone fastener 12 with tissue, as described herein. Surface 40 extends between an end 44 and an end 46. In some embodiments, passageway 42 extends longitudinally through bone fastener 12 such that bone fastener 12 is cannulated along the entire length of shaft 16 and tip 32, as shown in FIG. 4.

End 44 is connected with an axial opening 48 of head 100 disposed in communication with passageway 42. In some embodiments, opening 48 is in communication with a cavity 122 of receiver 114. In some embodiments, passageway 42 may be disposed in various orientations, such as, for example, perpendicular, transverse and/or at angular orientations, such as acute or obtuse relative to axis X1.

Portion 30 includes a plurality of lateral openings, such as, for example, fenestrations 50. Fenestrations 50 each define a lateral passageway that extends from passageway 42 through a wall thickness of portion 30 between surfaces 34, 40. Fenestrations 50 are in communication with passageway 42 such that the wall of portion 30 is closed exclusive of fenestrations 50. Fenestrations 50 facilitate a flow of an agent from passageway 42 into a vertebral body, as described herein. In some embodiments, fenestrations 50 are solely disposed in an axial alignment along passageway 42, as shown in FIG. 4. Portion 30 includes three equally spaced fenestrations 50. In some embodiments, fenestrations 50 are elongated and disposed in a serial orientation along passageway 42. In some embodiments, fenestrations 50 may be alternately configured, such as, for example, oval, triangular, square, polygonal, irregular, uniform, non-uniform and/or tapered.

Fenestrations 50 allow the flow of an agent disposed within passageway 42 external to shaft 16. In some embodiments, fenestrations 50 are configured to selectively disperse the agent in a uni-directional orientation to target deployment of the agent to selected tissue. In some embodiments, fenestrations 50 are configured to selectively disperse the agent to a selected tissue quadrant disposed about shaft 16. Selective orientation of shaft 16 and corresponding positioning of fenestrations 50 relative to targeted tissue provides directional control of dispersion of the agent. In some embodiments, such targeted deployment disperses the agent into healthier tissue to resist and/or prevent leakage of the agent from areas with diminished bone quality. Fenestrations 50 are disposed along a single side of shaft 16 to provide directional control of the disbursement of the agent to an area of healthy tissue and avoid areas of diminished bone quality. Shaft 16 can be rotated to position fenestrations 50 in alignment with targeted tissue and/or to an area of healthier tissue to avoid areas of diminished bone quality. In some embodiments, deployment of an agent from bone fastener 12, as described herein, consists of selective expulsion of the agent only from fenestrations 50.

Figure 3:
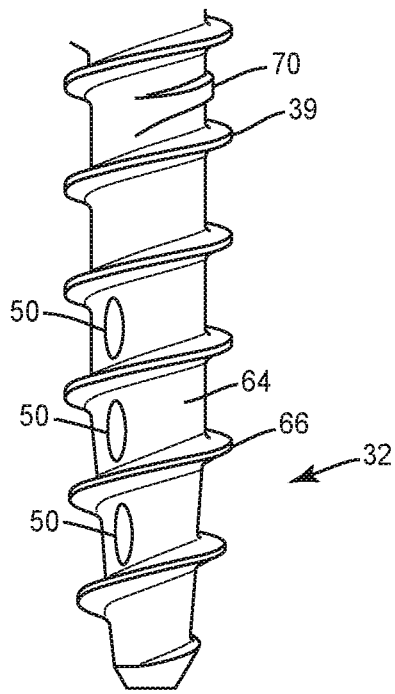
FIG. 3 is a break away view of the components shown in FIG. 2.
Figure 3A:
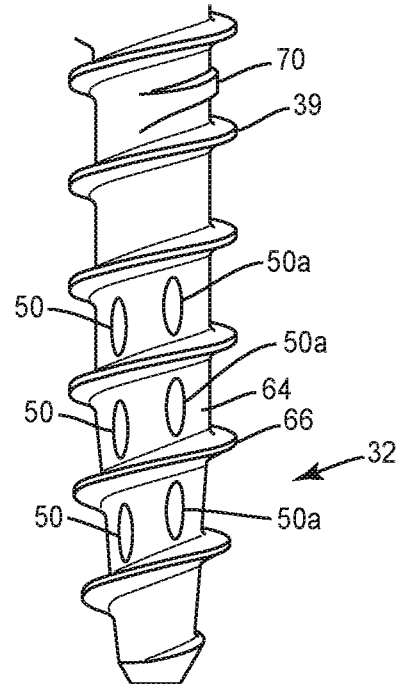
FIG. 3A is a break away view of components of one embodiment of a system in accordance with the principles of the present disclosure.

In some embodiments, fenestrations 50 are disposed perpendicular relative to passageway 42. In some embodiments, fenestrations 50 may be disposed at alternate orientations, relative to passageway 42, such as, for example, transverse and/or other angular orientations such as acute or obtuse, coaxial and/or may be offset or staggered. In some embodiments, fenestrations 50 include a tapered configuration. In one embodiment, as shown in FIG. 3A, shaft 16 includes an array of fenestrations 50 and an array of fenestrations 50*a*. Fenestrations 50, 50*a* are spaced apart, offset and disposed in a relatively parallel orientation along axis X1. Fenestrations 50, 50*a* provide deployment of the agent to selected tissue, for example, to a selected tissue quadrant disposed about shaft 16. In some embodiments, fenestrations 50, 50*a* are spaced apart along shaft 16 at a relative angular orientation of 60 degrees relative to axis X1.

In some embodiments, the agent may include bone growth promoting material, such as, for example, bone graft to enhance fixation of bone fastener 12 and/or other components of a spinal construct with tissue, as described herein. Osteogenic material may be included in the agent such as, for example, autologous bone harvested from the patient receiving the implant device, bone allograft, bone xenograft, any number of non-bone implants (for example ceramic, metallic, polymer), bone morphogenic protein, and/or bio-resorbable compositions. In some embodiments, the agent can contain other bioactive agents or other active agents, which may include one or a plurality of therapeutic agents and/or pharmacological agents for release, including sustained release, into a vertebra to treat, for example, pain, inflammation and degeneration. The agents may include pharmacological agents, such as, for example, antibiotics, pain medications, analgesics, anesthetics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof. In some embodiments, the agent may include bone cement that enhances fixation of bone fastener 12 with tissue. In some embodiments, the bone cement may include a poly(methyl methacrylate) (PMMA); methyl methacrylate (MMA); calcium phosphate; a resorbable polymer, such as, for example, PLA, PGA or combinations thereof; a resorbable polymer with allograft, such as, for example, particles or fibers of mineralized bone and/or combinations thereof.

Tip 32 includes a surface 60 that defines a passageway 62. Passageway 62 is disposed in communication with passageway 42 such that tip 32 is cannulated to allow an agent, as described herein, to flow from tip 32. In some embodiments, an agent is selectively expelled to targeted tissue via uni-directional deployment from fenestrations 50, as described herein, and through passageway 62 in a targeted deployment from tip 32. In some embodiments, deployment of an agent from bone fastener 12, as described herein, consists of selective expulsion of the agent only from fenestrations 50 and tip 32. In some embodiments, tip 32 is tapered, for example, with a bevel for easier insertion and less tearing of the tissue. In some embodiments, tip 32 includes a tapered configuration to define an awl tip to facilitate self-tapping for engagement with vertebrae. In some embodiments, tip 32 has a blunt configuration. In some embodiments, tip 32 includes a sharpened point.

Figure 7:
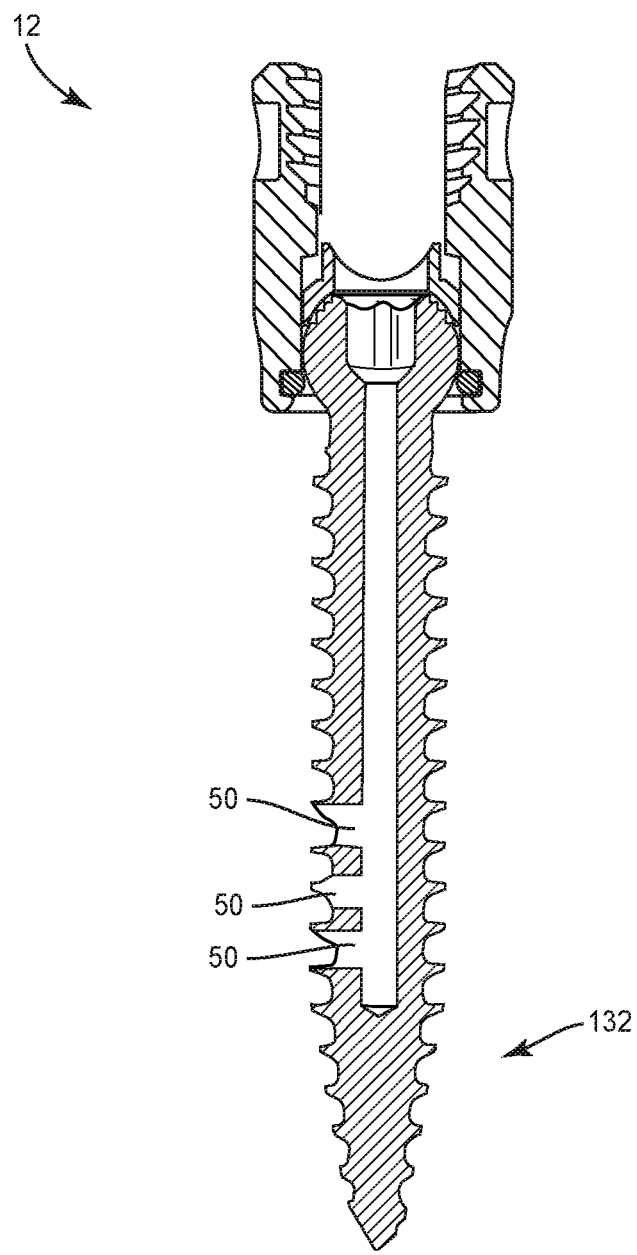
FIG. 7 is a side view of components of one embodiment of a system in accordance with the principles of the present disclosure.

Tip 32 includes a surface 64 having a thread 66. Thread 66 is oriented with tip 32 and disposed for engagement with tissue. Thread 66 is continuous with thread 39 along tip 32 and includes a similar configuration. In some embodiments, thread 66 may be alternatively configured, similar to threads 36, 39, described herein. In some embodiments, surface 64 is oriented at an angle in a range of 0 through 15 degrees relative to axis X1. In some embodiments, bone fastener 12 includes a tip 132 having a solid, non-cannulated configuration, as shown in FIG. 7, such that deployment of an agent from bone fastener 12, as described herein, consists of selective expulsion of the agent only from fenestrations 50, as described herein, to targeted tissue.

In some embodiments, shaft 16 includes a resistance element, such as, for example, a thread 70. Thread 70 extends along a portion of surface 34 between adjacent crests of thread 39, as shown in FIGS. 1 and 3. Thread 70 is separate and spaced apart from thread 39. In some embodiments, thread 70 extends in a parallel orientation relative to thread 39. In some embodiments, thread 70 may extend transverse, convergent, divergent, intersecting, staggered and/or offset relative to the thread 39.

In some embodiments, the resistance element, such as, for example, thread 70 is configured to increase an insertion torque upon engagement of thread 70 with tissue, such as, for example, bone and/or a spinal implant, such as, for example, a cervical plate. The increase in torque generates and/or provides tactile indicia to a practitioner that bone fastener 12 is approaching a portion of shaft 16, such as, for example, thread 36 during engagement with bone and/or a spinal implant. In one embodiment, thread 70 engages tissue and/or a spinal implant to increase an insertion torque of bone fastener 12 for generating and/or providing tactile indicia to a practitioner between a first and/or initial position and a second position. In some embodiments, the tactile indicia may comprise position indicia of bone fastener 12 and/or engagement of thread 70 with tissue and/or a spinal implant may generate position indicia alone.

Figure 5:
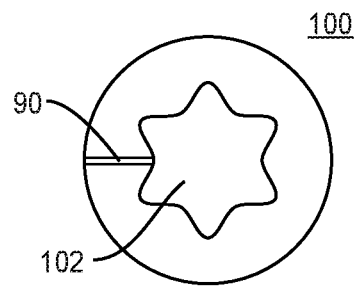
FIG. 5 is a top view of components of one embodiment of a system in accordance with the principles of the present disclosure.

Head 100 includes a socket 102 configured for engagement with a drive surface of a surgical driver instrument, as described herein. Socket 102 defines a hexalobular cross section for disposal and engagement of a correspondingly shaped portion of the drive surface. In some embodiments, socket 102 defines a cruciform, phillips, square, polygonal or star cross sectional configuration for disposal and engagement of a correspondingly shaped portion of the drive surface. The surface of head 100 defining socket 102 comprises a portion of a torque interface between a surgical instrument to drive, rotate, torque, insert, implant or otherwise connect bone fastener 12 with tissue, as described herein. In one embodiment, as shown in FIG. 5, head 100 includes indicia, such as, for example, a marker 90 that displays the orientation of deployment of the agent from fenestrations 50 with tissue. Marker 90 displays the orientation of a uni-directional agent deployment, which enables more controlled placement of the agent and/or locating fenestrations 50 and their orientation with tissue. In some embodiments, marker 90 is disposed with socket 102. In some embodiments, the indicia may include visual indicia, tactile indicia, audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, the indicia includes a notch, slot, bead, detent, bump, print, label, score, color coding and/or cavity disposed on shaft 16. In some embodiments, the indicia may be attachable with or adhered to shaft 16. In some embodiments, the indicia may be disposed with a surgical instrument engageable with socket 102 and aligned with fenestrations 50 and/or marker 90. In some embodiments, marker 90 may be employed to display the orientation of deployment of the agent from shaft 16 including fenestrations 50, 50a with tissue.

Bone fastener 12 includes an implant receiver 114 connectable with shaft 16. Receiver 114 extends along and defines an axis X2. Receiver 114 includes a pair of spaced apart arms 118, 120 that define an implant cavity 122 therebetween configured for disposal of a component of a spinal construct, such as, for example, a spinal rod (not shown). Arms 118, 120 extend parallel to axis X2. In some embodiments, arm 118 and/or arm 120 may be disposed at alternate orientations, relative to axis X2, such as, for example, transverse, perpendicular and/or other angular orientations such as acute or obtuse, coaxial and/or may be offset or staggered. Arms 118, 120 each include an arcuate outer surface extending between a pair of side surfaces. At least one of the outer surfaces and the side surfaces of arms 118, 120 have at least one recess or cavity therein configured to receive an insertion tool, compression instrument and/or instruments for inserting and tensioning bone fastener 12. In some embodiments, arms 118, 120 are connected at proximal and distal ends thereof such that receiver 114 defines a closed spinal rod slot. In some embodiments, such as for a fixed axis screw, a sagitally adjusting screw, or a transverse and sagitally adjusting screw, the marker 90 may be located on the receiver 114 when the receiver 114 is in a fixed rotational orientation with respect to the shaft 16.

Cavity 122 is substantially U-shaped. In some embodiments, all or only a portion of cavity 122 may have alternate cross section configurations, such as, for example, closed, V-shaped, W-shaped, oval, oblong triangular, square, polygonal, irregular, uniform, non-uniform, offset, staggered, and/or tapered. Receiver 114 includes an inner surface 124. A portion of surface 124 includes a thread form 126. Thread form 126 is configured for engagement with a coupling member, such as, for example, a setscrew (not shown), to retain a spinal rod within cavity 122. In some embodiments, surface 124 may be disposed with the coupling member in alternate fixation configurations, such as, for example, friction fit, pressure fit, locking protrusion/recess, locking keyway and/or adhesive. In some embodiments, all or only a portion of surface 124 may have alternate surface configurations to enhance engagement with a spinal rod and/or the setscrew, such as, for example, rough, arcuate, undulating, mesh, porous, semi-porous, dimpled and/or textured. In some embodiments, receiver 14 may include alternate configurations, such as, for example, closed, open and/or side access.

In some embodiments, receiver 114 is connectable with shaft 16 to form a multi-axial screw (MAS). In some embodiments, connection of receiver 114 with shaft 16 can be actuated by a manual engagement and/or non-instrumented assembly, which may include a practitioner, surgeon and/or medical staff grasping receiver 114 and shaft 16 and forcibly snap or pop fitting the components together. In some embodiments, receiver 114 is connectable with shaft 16 to include various configurations, such as, for example, a uni-axial screw (UAS), a fixed angle screw (FAS), a side loading screw, a sagittal adjusting screw (SAS), a transverse sagittal adjusting screw (TSAS), an awl tip screw (ATS) or a sacral bone screw.

Figure 6:
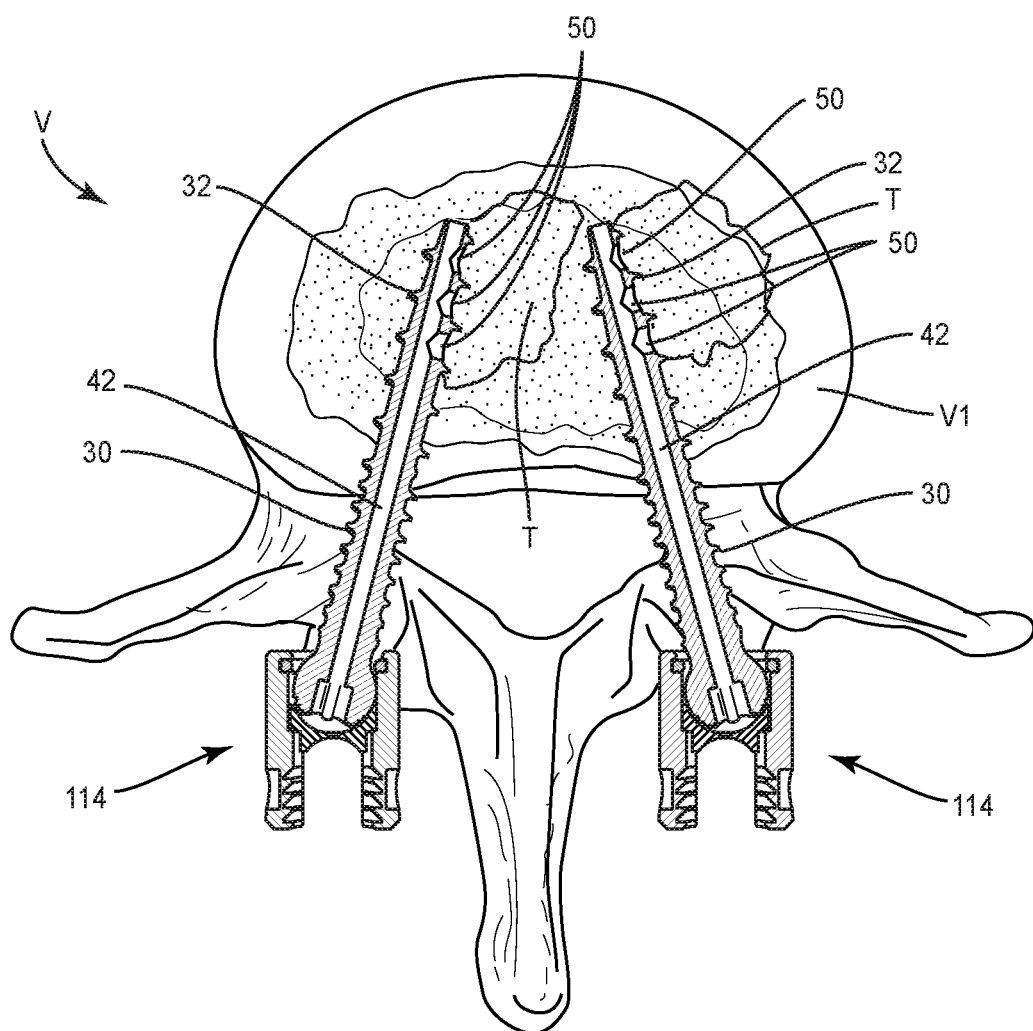
FIG. 6 is an axial view of components of one embodiment of a system in accordance with the principles of the present disclosure disposed with a spine.

In assembly, operation and use, spinal implant system 10, similar to the systems and methods described herein, includes bone fastener 12 and is employed with a surgical procedure for treatment of a spinal disorder affecting a section of a spine of a patient, as discussed herein. The components of spinal implant system 10 are employed with a surgical procedure for treatment of a condition or injury of an affected section of the spine, such as, for example, vertebrae V, as shown in FIG. 6.

In use, to treat a selected section of vertebrae V, a medical practitioner obtains access to a surgical site including vertebrae V. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region.

Pilot holes are made in a vertebral level V1 of vertebrae V in a selected orientation for disposal of one or more bone fasteners 12. Bone fasteners 12 are engaged with a surgical driver instrument, as described herein, for orientation and disposal with the pilot holes. Each bone fastener 12 is aligned with the pilot hole and the driver is torqued or otherwise rotated such that shaft 16 translates axially within the pilot hole for engagement with the tissue of vertebral level V1.

Shaft 16 is rotated causing threads 66, 39, 36, as described herein, to engage tissue of vertebra V1. Shaft 16 is rotated to a selected orientation relative to tissue of vertebra V1 such that fenestrations 50 are positioned relative to targeted tissue T to provide directional control and expulsion of the agent to tissue T and/or adjacent areas of vertebrae V, as described herein. In some embodiments, marker 90 displays and/or locates the orientation of fenestrations 50 and/or agent deployment with tissue, as described herein. An injection device, such as, for example, a syringe or a pump including a port for connection with opening 48 is connected with a source of an agent, as described herein. The agent is provided to bone fastener 12 via the injection device for transfer to passageway 42.

The agent flows through passageway 42 and is selectively directed and/or guided for expulsion through fenestrations 50 to tissue T and/or through passageway 62 in a targeted deployment from tip 32. Fenestrations 50 are solely disposed along a side of shaft 16 in a serial and/or axial configuration to provide uni-directional deployment of the agent to tissue T, which can include healthy tissue and avoid areas of diminished bone quality. In some embodiments, selective deployment of the agent to tissue T targets healthier, less degenerated tissue to resist and/or prevent leakage of the agent outside vertebra V1. In some embodiments, deployment of the agent from bone fastener 12, as described herein, consists of selective expulsion of the agent only from fenestrations 50. In some embodiments, deployment of the agent from bone fastener 12, as described herein, consists of selective expulsion of the agent only from fenestrations 50 and tip 32.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of rods, plates, connectors and/or bone fasteners for use with a single vertebral level or a plurality of vertebral levels.

In some embodiments, spinal implant system 10 comprises a kit including a plurality of bone fasteners 12 of varying configuration, as described herein. In some embodiments, bone fastener 12 is selected from the kit for employing with a treatment at the surgical site. In some embodiments, bone fastener 12 is connected with a surgical instrument to facilitate insertion and manipulation of bone fastener 12 utilizing an image guide, such as, for example, a navigation component (not shown) of a medical imaging and navigation system (not shown), as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
a shaft having a distal tip and the shaft including a wall, the wall defining a longitudinal cavity and openings in communication with the longitudinal cavity, the wall being closed exclusive of the openings, the openings including a first array of openings disposed in axial alignment along the shaft and extending along a first longitudinal axis, the openings including a second array of openings disposed in axial alignment along the shaft and extending along a second longitudinal axis, the second longitudinal axis being offset from the first longitudinal axis, the second array of openings being spaced apart from the first array of openings within a 90 degree quadrant of the shaft such that the openings are entirely within the 90 degree quadrant of the shaft.

2. A bone fastener as recited in claim 1, wherein the arrays of openings each include a plurality of lateral fenestrations disposed in a serial orientation along the wall.

3. A bone fastener as recited in claim 1, wherein the arrays of openings each include three equally spaced lateral fenestrations disposed in a serial orientation adjacent a distal surface of the shaft.

4. A bone fastener as recited in claim 1, wherein the distal tip is closed.

5. A bone fastener as recited in claim 1, wherein the longitudinal cavity extends through the distal tip of the shaft.

6. A bone fastener as recited in claim 1, wherein the distal tip has a tapered configuration.

7. A bone fastener as recited in claim 1, wherein the distal tip has a blunt configuration.

8. A bone fastener as recited in claim 1, wherein the shaft includes a cannulated proximal portion.

9. A bone fastener as recited in claim 1, wherein the wall includes a proximal end that defines an axial opening disposed in communication with the longitudinal cavity.

10. A bone fastener as recited in claim 1, wherein the first array of openings is spaced apart along the shaft at an angular orientation of 60 degrees relative to a longitudinal axis defined by the longitudinal cavity.

11. A bone fastener as recited in claim 1, wherein the first and second longitudinal axes each extend parallel to the longitudinal cavity.

12. A bone fastener as recited in claim 1, wherein the second array of openings is spaced apart from the first array of openings about a circumference of the shaft.

13. A bone fastener comprising:
a head; and
a threaded shaft including a wall defining an inner surface and an outer surface, the inner surface defining a longitudinal cavity and fenestrations disposed between threads of the threaded shaft, the fenestrations each being in communication with the longitudinal cavity, the wall being closed exclusive of the fenestrations, the fenestrations each being tapered, the fenestrations including a first array of fenestrations disposed in axial alignment along the threaded shaft and extending along a first longitudinal axis, the fenestrations including a second array of fenestrations disposed in axial alignment along the threaded shaft and extending along a second longitudinal axis, the second longitudinal axis being spaced apart from the first longitudinal axis within a 90 degree quadrant of the threaded shaft such that the fenestrations are entirely within the 90 degree quadrant of the threaded shaft.

14. A bone fastener as recited in claim 13, wherein the head is removably coupled to the threaded shaft such that the threaded shaft is rotatable relative to the head in a multi-axial configuration.

15. A bone fastener comprising:
an implant receiver; and
a shaft defining a longitudinal cavity and openings in communication with the longitudinal cavity, the shaft including a proximal end surface and an opposite distal end surface, the openings including a first array of openings disposed in axial alignment along the shaft and extending along a first longitudinal axis, the openings including a second array of openings disposed in axial alignment along the shaft and extending along a second longitudinal axis, the second longitudinal axis being offset from the first longitudinal axis, the second array of openings being spaced apart from the first array of openings within a 90 degree quadrant of the shaft such that the openings are entirely within the 90 degree quadrant of the shaft, the end surfaces each extending perpendicular to a longitudinal axis defined by the longitudinal cavity, the shaft further including a slot extending into the proximal end surface to display an orientation of the first array of openings for deployment of an agent with tissue.

16. A bone fastener as recited in claim 15, wherein the implant receiver is rotatable relative to the shaft in a multi-axial configuration.

17. A bone fastener as recited in claim 15, wherein the implant receiver is rotatable relative to the shaft in a sagittal adjustable configuration.

18. A bone fastener as recited in claim 15, wherein the arrays of openings are configured to selectively expel the agent in a uni-directional orientation with the tissue.

19. A bone fastener as recited in claim 15, wherein the arrays of openings each include three equally spaced lateral fenestrations disposed in a serial orientation adjacent a distal surface of the shaft.

20. A bone fastener as recited in claim 15, wherein the openings each extend perpendicular to a longitudinal axis defined by the longitudinal cavity.

* * * * *